United States Patent
Kempen et al.

(10) Patent No.: US 11,708,374 B2
(45) Date of Patent: Jul. 25, 2023

(54) PREPARATION OF CONDENSED TRIAZEPINE DERIVATIVES AND THEIR USE AS BET INHIBITORS

(71) Applicant: DYBLY AG, Basel (CH)

(72) Inventors: Herman Kempen, Schöftland (CH); Adel Far, Saint-Laurent (CA)

(73) Assignee: WORG PHARMACEUTICALS (ZHEJIANG) CO., LTD., Huzhou (CN)

( * ) Notice: Subject to any disclaimer, the term of this patent is extended or adjusted under 35 U.S.C. 154(b) by 175 days.

(21) Appl. No.: 17/122,744

(22) Filed: Dec. 15, 2020

(65) Prior Publication Data

US 2021/0101909 A1  Apr. 8, 2021

Related U.S. Application Data

(63) Continuation of application No. 16/811,311, filed on Mar. 6, 2020, now Pat. No. 10,906,917, which is a continuation of application No. PCT/EP2019/064935, filed on Jun. 7, 2019.

(30) Foreign Application Priority Data

Jun. 13, 2018 (EP) .................................. 18177511

(51) Int. Cl.
*C07D 495/14* (2006.01)
*A61K 31/55* (2006.01)
*A61P 29/00* (2006.01)
*A61P 35/00* (2006.01)

(52) U.S. Cl.
CPC ............ *C07D 495/14* (2013.01); *A61P 35/00* (2018.01)

(58) Field of Classification Search
CPC ....... C07D 495/14; A61K 31/55; A61P 29/00; A61P 35/00
See application file for complete search history.

(56) References Cited

U.S. PATENT DOCUMENTS

| | | | |
|---|---|---|---|
| 4,155,913 | A | 5/1979 | Hellerbach et al. |
| 5,712,274 | A | 1/1998 | Sueoka et al. |
| 5,721,231 | A | 2/1998 | Moriwaki et al. |
| 5,760,032 | A | 6/1998 | Kitajima et al. |
| 5,807,850 | A | 9/1998 | Nakamura et al. |
| 6,444,664 | B1 | 9/2002 | Princen et al. |
| 2010/0041643 | A1 | 2/2010 | Adachi et al. |
| 2013/0184264 | A1 | 7/2013 | Bradner et al. |
| 2015/0174138 | A1 | 6/2015 | Bernstein et al. |
| 2017/0209461 | A1 | 7/2017 | Landau et al. |
| 2017/0360801 | A1 | 12/2017 | Sotomayor et al. |

FOREIGN PATENT DOCUMENTS

| | | |
|---|---|---|
| CN | 103694253 A | 4/2014 |
| EP | 0176927 | 4/1986 |
| EP | 0792880 | 9/1997 |
| EP | 0934940 | 8/1999 |
| EP | 0989131 | 3/2000 |
| EP | 2239264 | 10/2010 |
| JP | 3633008 | 3/2005 |
| WO | WO-97/09048 | 3/1997 |
| WO | WO-97/47622 | 12/1997 |
| WO | WO-2008/092231 | 8/2008 |
| WO | WO-2009/158404 | 12/2009 |
| WO | WO-2010/049466 | 5/2010 |
| WO | WO-2010/079431 | 7/2010 |
| WO | WO-2011/143660 | 11/2011 |
| WO | WO-2011/143669 | 11/2011 |
| WO | WO-2014/159392 | 10/2014 |
| WO | WO-2015/018522 | 2/2015 |
| WO | WO-2015/078929 | 6/2015 |
| WO | WO-2015/078931 | 6/2015 |
| WO | WO-2015/156601 | 10/2015 |
| WO | WO-2015/168621 | 11/2015 |
| WO | WO-2015/189814 | 12/2015 |
| WO | WO-2016/069578 | 5/2016 |
| WO | WO-2018/221679 | 12/2018 |

OTHER PUBLICATIONS

Bailey et al., "RVX-208: A Small Molecule That Increases Apolipoprotein A-I and High-Density Lipoprotein Cholesterol In Vitro and In Vivo," Am. Coll. Cardiol., 55(23), pp. 2580-2589 (2010).

Chung et al., "Discovery and Characterization of Small Molecule Inhibitors of the BET Family Bromodomains," J. Med. Chem., 54, pp. 3827-3838 (2011).

Dawson et al., "Inhibition of BET recruitment to chromatin as an effective treatment for MLL-fusion leukaemia," Nature, 478, pp. 529-533 (2011).

Deepak et al., "In silico design and bioevaluation of selective benzotriazepine BRD4 inhibitors with potent antiosteoclastogenic activity," Chem. Biol. Drug Des., 90, pp. 97-111 (2017).

Delmore et al., "BET bromodomain inhibition as a therapeutic strategy to target c-Myc," Cell, 146, pp. 904-917 (2011).

Ding et al., "BRD4 is a novel therapeutic target for liver fibrosis," PNAS, 112(51), pp. 15713-15718 (2015).

Filippakopoulos et al., "Benzodiazepines and benzotriazepines as protein interaction inhibitors targeting bromodomains of the BET family," Bioorganic & Medicinal Chemistry, 20, pp. 1878-1886 (2012).

(Continued)

*Primary Examiner* — Brenda L Coleman
(74) *Attorney, Agent, or Firm* — Mintz Levin Cohn Ferris Glovsky and Popeo, P.C.

(57) ABSTRACT

The invention relates to compounds of the formula:

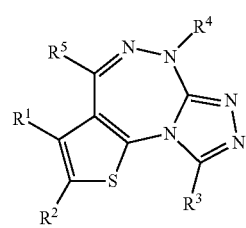

and pharmaceutically acceptable salts thereof. These compounds are useful in the treatment of inflammatory diseases, fibrotic diseases and neoplastic diseases.

23 Claims, 3 Drawing Sheets

(56) References Cited

OTHER PUBLICATIONS

Filippakopoulos et al., "Selective inhibition of BET bromodomains," (76 pages total including appendix), Author Manuscript, published in final edited form as: Nature, 468(7327), pp. 1067-1073 (2010).

Kempen et al., "Stimulation of Hepatic Apolipoprotein A-I Production by Novel Thieno-Triazolodiazepines: Roles of the Classical Benzodiazepine Receptor, PAF Receptor, and Bromodomain Binding," Lipid Insights, 6, pp. 47-54 (2013).

Klein, "Bromodomain protein inhibition: a novel therapeutic strategy in rheumatic diseases," RMD Open, 4(2), pp. 1-10 (2018).

Mertz et al., "Targeting MYC dependence in cancer by inhibiting BET bromodomains," Proc. Natl. Acad. Sci. USA, 108(40), pp. 16669-16674 (2011).

Nicholls et al., "Efficacy and Safety of a Novel Oral Inducer of Apolipoprotein A-I Synthesis in Statin-Treated Patients With Stable Coronary Artery Disease: A Randomized Controlled Trial," J. Am. Coll. Cardiol., 57(9), pp. 1111-1119 (2011).

Nicodeme et al., "Suppression of inflammation by a synthetic histone mimic," (45 pages total including Supplementary Information), Nature, 468, pp. 1119-1123 (2010).

Philpott et al., "Bromodomain-peptide displacement assays for interactome mapping and inhibitor discovery," (16 pages total including appendix), Mol. BioSyst., 7, pp. 2899-2908 (2011).

Zanotti et al., "The thienotriazolodiazepine Ro 11-1464 increases plasma apoA-I and promotes reverse cholesterol transport in human apoA-I transgenic mice," Br. J. Pharmacol., 164, pp. 1642-1651 (2011).

International Search Report and Written Opinion for International Patent Application No. PCT/EP2019/064935, dated Aug. 19, 2019 (12 pages).

PREPARATION OF CONDENSED TRIAZEPINE DERIVATIVES AND THEIR USE AS BET INHIBITORS

CROSS-REFERENCES TO RELATED APPLICATIONS

This application is a continuation of U.S. application Ser. No. 16/811,311, filed Mar. 6, 2020, which is a continuation of PCT International Application No. PCT/EP2019/064935, filed on Jun. 7, 2019, which is an International Application of and claims the benefit of priority to European Patent Application No. 18177511.5, filed on Jun. 13, 2018, the entire contents of which are herein incorporated by reference.

FIELD OF THE INVENTION

The invention relates to the field of bromodomain inhibiting thienotriazolotriazepine compounds, to pharmaceutical composition comprising such compounds, and the use of the compounds for treatment or prevention of inflammatory, fibrotic and neoplastic diseases.

BACKGROUND

Bromodomain-containing proteins have been implicated as targets in human cancer, inflammation, fibrotic diseases, rheumatic diseases, asthma, coronary artery and cardiovascular disease, Alzheimer's disease, autism-like syndrome, graft-versus-host disease and a variety of autoimmune conditions (Kertin Klein. "Bromodomain protein inhibition: a novel therapeutic strategy in rheumatic diseases", Rheumatic and Musculosketal Diseaes Open, 2018; 4(2), doi: 10.1136/rmdopen-2018-000744). The Bromodomain and extraterminal domain (BET) family include proteins BRD2, BRD3, BRD4 and BRDT which are proteins interacting with acetylated histones H3/H4. BET proteins are known to modulate expression of genes involved in inflammation, cell proliferation and fibrosis.

BET inhibitors are compounds that reversibly bind to BET proteins and thereby prevent interaction between the BET protein and acetylated lysine residues in histones and transcription factors.

We have shown previously that compounds in the thienotriazolodiazepine class, are able to increase ApoAl production in human hepatocytes; WO 97/09048, WO 2010/049466 and Kempen et al, Lipid Insights 2013, 6: 47-54.

WO 2011/143669 A2 relates to thienotriazolodiazepines, for instance (+)JQ1, for use as BET inhibitors in the treatment of neoplasia and inflammatory diseases.

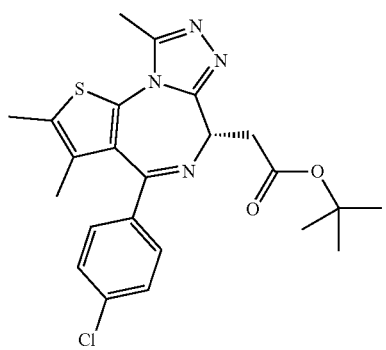

(+)JQ1

EP 2 239 264 A1 and WO 2014/159392 also relates to thienotriazolodiazepines for use as BET inhibitors.

Triazolobenzodiazepines and triazolobenzotriazepines have been found to act as BET bromodomain inhibitors due to their structural similarity to acetylated lysine residues (Chung et al, J. Med Chem 2011; 54:3827-3838; Filippakopoulos et al. Nature 2010 468:1067-1073; Nicodeme et al, Nature 2010 468:1119-1123, Filippakopoulos et al, Bioorg Med Chem. 2012 20:1878-1886) and to have potential as anti-inflammatory and antineoplastic agents This work provided a crystallographic structure of the complex of the bromodomain protein with the above mentioned diazepines and thereby enabled a rational approach to the design of more potent compounds. Furthermore, such azepines and non-azepine BRD4 inhibitors were shown to suppress proliferation of myeloma cells by targeting expression of the oncogene c-Myc (Merz et al Proc Natl Acad Sci USA 2011:108:16669-74; Delmore et al Cell 146, 904-917, 2011, Dawson et al, Nature 478, 529-539, 2011).

There remains a need for improved BET inhibitors, particularly compounds having higher potency as bromodomain inhibitors and which therefore may have a useful therapeutic window in vivo, particularly for use in the treatment of cancer, inflammation and fibrotic diseases.

BRIEF DESCRIPTION OF THE INVENTION

It has been found that compounds of general formula I

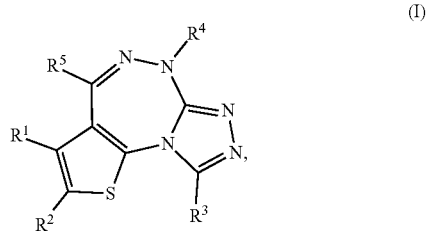

(I)

or pharmaceutically acceptable salts thereof, wherein $R^1$ to $R^5$ are as defined below, are effective and potent bromodomain inhibitors (BET inhibitors). The invention accordingly provides compounds of formula I, methods for the preparation of compounds of formula I, and pharmaceutical compositions comprising compounds of formula I. Particularly, compounds of formula (I) are useful as BRD4 inhibitors. Thus, the invention relates to compounds of formula (I) for use as a medicament.

The invention also relates to compounds of formula (I) for use in the treatment or prevention of an inflammatory disease, a fibrotic disease or a neoplastic disease, such as cancer, in particular blood cancer (leukemia) in a subject in need thereof.

The invention further provides compounds of formula (I) for use in manufacturing a medicament for the treatment of an inflammatory disease, a fibrotic disease or a neoplastic disease in a subject in need thereof.

The invention also relates to a method of treating an inflammatory disease, a fibrotic disease or a neoplastic disease in a subject in need thereof, the method comprising administering to the subject a therapeutically effective amount of a compound of formula (I), or a pharmaceutically acceptable salt thereof.

DETAILED DESCRIPTION OF THE INVENTION

Figure 1A:
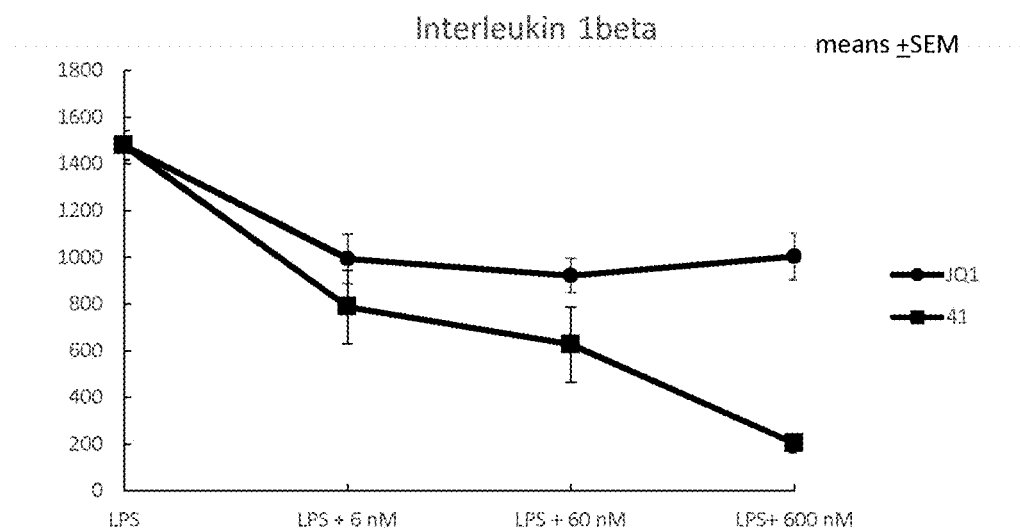
FIGS. 1A, 1B and 1C illustrate the effect of "Compound 41" (Example 2) and of reference compound (+)JQ1 on Lipopolysaccharide (LPS)-stimulated interleukin-1beta, interleukin-6 and tumor necrosis factor-alpha in human full blood.

The invention provides compounds having the following formula (I)

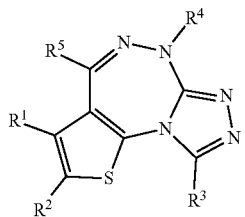
(I)

or a pharmaceutically acceptable salt thereof;
wherein:
$R^1$ and $R^2$ are each independently selected from the group consisting of a hydrogen, a halogen and ($C_1$-$C_6$) alkyl;
$R^3$ is selected from the group consisting of ($C_1$-$C_6$) alkyl, —OH and halogen;
$R^4$ is selected from the group consisting of ($C_1$-$C_6$) alkyl and

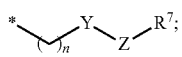

$R^5$ is selected from the group consisting of an aryl, a heteroaryl, a benzodioxolane and a benzodioxane, wherein said aryl, heteroaryl, benzodioxolane or benzodioxane is optionally substituted with a halogen or a ($C_1$-$C_4$) alkoxy group;
each $R^7$ is independently hydrogen or ($C_1$-$C_6$) alkyl;
—Y—Z— is selected from the group consisting of —C(O)—O—, —O—C(O)— and —C(O)—N($R^7$)—; and
each n is independently 0 or a natural integer ≤4, such as 1, 2, 3 or 4.

In embodiments of compounds of Formula (I), $R^5$ is selected from the group of

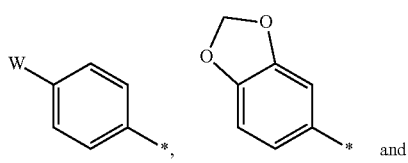

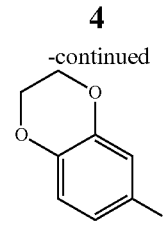

wherein W is a halogen, such as such as fluorine, chlorine, bromine or iodine.

In embodiments of compounds of Formula (I), $R^5$ is selected from the group consisting of an aryl and a heteroaryl, each optionally substituted with a halogen or a ($C_1$-$C_4$) alkoxy group.

In embodiments of compounds of Formula (I), $R^5$ is an aryl, optionally substituted with a halogen or a ($C_1$-$C_4$) alkoxy group.

In embodiments of compounds of Formula (I), $R^5$ is phenyl, optionally substituted with a halogen or a ($C_1$-$C_4$) alkoxy group.

In embodiments of compounds of Formula (I), $R^5$ is phenyl substituted with a halogen or a ($C_1$-$C_4$) alkoxy group.

In embodiments, compounds of Formula (I) are compounds of Formula (II), or a pharmaceutically acceptable salt thereof:

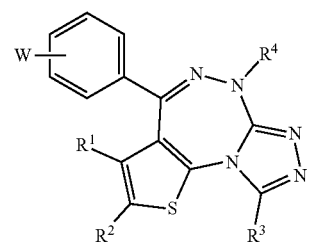
(II)

wherein W is a halogen (such as fluorine, chlorine, bromine or iodine), in particular W is chlorine.

In embodiments, compounds of Formula (I) are compounds of Formula (IIa), or a pharmaceutically acceptable salt thereof:

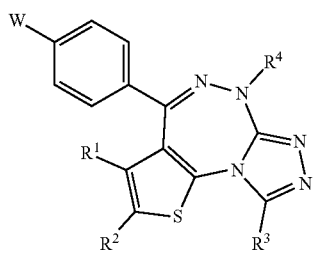
(IIa)

wherein W is a halogen (such as fluorine, chlorine, bromine or iodine), in particular W is chlorine.

In embodiments of compounds of Formula (I), (II) or (IIa), $R^4$ is ($C_1$-$C_6$) alkyl.

In embodiments of compounds of Formula (I), (II) or (IIa), $R^4$ is ($C_1$-$C_4$) alkyl, such as methyl, ethyl, n-propyl, 1-methylethyl, n-butyl, 1-methylpropyl, 2-methylpropyl or 1,1-dimethylethyl (tert-butyl).

In embodiments of compounds of Formula (I), (II) or (IIa), $R^4$ is methyl.

In embodiments of compounds of Formula (I), (II) or (IIa), $R^4$ is

*—(CH$_2$)$_n$—Y—Z—R$^7$.

In embodiments of compounds of Formula (I), (II) or (IIa), n is 0.

In embodiments of compounds of Formula (I), (II) or (IIa), n is 1, 2, 3 or 4.

In embodiments of compounds of Formula (I), (II) or (Ia), n is 1, 2 or 3.

In embodiments of compounds of Formula (I), (II) or (IIa), n is 1 or 2.

In embodiments of compounds of Formula (I), (II) or (IIa), n is 1.

In embodiments of compounds of Formula (I), (II) or (IIa), $R^4$ is selected from the group of

*—CH$_2$—C(O)—NH—R$^7$  and  *—CH$_2$—C(O)—O—R$^7$.

In embodiments of compounds of Formula (I), (II) or (IIa), $R^4$ is selected from the group consisting of ($C_1$-$C_4$) alkyl and

*—(CH$_2$)$_n$—Y—Z—R$^7$, where —Y—Z— is —C(O)—O—, n is 1 or 2, and $R^7$ is hydrogen or ($C_1$-$C_4$) alkyl.

In embodiments of compounds of Formula (I), (II) or (IIa), $R^4$ is ($C_1$-$C_4$) alkyl or

*—CH$_2$—C(O)—O—R$^7$.

In embodiments of compounds of Formula (I), (II) or (IIa), $R^4$ is

*—CH$_2$—C(O)—O—R$^7$.

In embodiments of compounds of Formula (I), (II) or (IIa), $R^4$ is

*—CH$_2$—C(O)—O—R$^7$ and $R^7$ is ($C_1$-$C_6$) alkyl, in particular ($C_1$-$C_4$) alkyl.

In embodiments of compounds of Formula (I), (II) or (IIa), $R^7$ is hydrogen or ($C_1$-$C_4$) alkyl.

In embodiments of compounds of Formula (I), (II) or (IIa), $R^7$ is hydrogen.

In embodiments of compounds of Formula (I), (II) or (IIa), $R^7$ is ($C_1$-$C_6$) alkyl.

In embodiments of compounds of Formula (I), (II) or (IIa), $R^7$ is ($C_1$-$C_4$) alkyl, such as methyl, ethyl, n-propyl, 1-methylethyl, n-butyl, 1-methylpropyl, 2-methylpropyl or 1,1-dimethylethyl (tert-butyl).

In embodiments of compounds of Formula (I), (II) or (IIa), $R^7$ is selected from the group consisting of hydrogen, methyl, ethyl, iso-propyl (1-methylethyl) and tert-butyl (1,1-dimethylethyl).

In embodiments of compounds of Formula (I), (II) or (IIa), $R^7$ is selected from the group consisting of methyl, ethyl, iso-propyl and tert-butyl.

In embodiments of compounds of Formula (I), (II) or (IIa), $R^7$ is methyl or ethyl.

In embodiments of compounds of Formula (I), (II) or (IIa), $R^4$ is ($C_1$-$C_4$) alkyl or

*—CH$_2$—C(O)—O—R$^7$ and $R^7$ is selected from the group consisting of hydrogen, methyl, ethyl, iso-propyl (1-methylethyl) and tert-butyl (1,1-dimethylethyl).

In embodiments of compounds of Formula (I), (II) or (IIa), $R^4$ is

*—CH$_2$—C(O)—O—R$^7$ and $R^7$ is selected from the group consisting of hydrogen, methyl, ethyl, iso-propyl (1-methylethyl) and tert-butyl (1,1-dimethylethyl).

In embodiments of compounds of Formula (I), (II) or (IIa), $R^1$ and $R^2$ are each independently selected from ($C_1$-$C_6$) alkyl.

In embodiments of compounds of Formula (I), (II) or (IIa), $R^1$ and $R^2$ are each independently selected from ($C_1$-$C_3$) alkyl, such as $R^1$ and $R^2$ are each independently selected from the group consisting of methyl, ethyl, n-propyl and 1-methylethyl (iso-propyl).

In embodiments of compounds of Formula (I), (II) or (IIa), $R^1$ and $R^2$ are each independently selected from methyl and ethyl.

In embodiments of compounds of Formula (I), (II) or (IIa), $R^1$ and $R^2$ are each ethyl.

In embodiments of compounds of Formula (I), (II) or (IIa), one of $R^1$ and $R^2$ is ethyl and one of $R^1$ and $R^2$ is methyl.

In embodiments of compounds of Formula (I), (II) or (IIa), $R^1$ and $R^2$ are each methyl.

In embodiments of compounds of Formula (I), (II) or (IIa), $R^3$ is ($C_1$-$C_6$) alkyl.

In embodiments of compounds of Formula (I), (II) or (IIa), $R^3$ is ($C_1$-$C_3$) alkyl, such as methyl, ethyl, n-propyl or 1-methylethyl (iso-propyl).

In embodiments of compounds of Formula (I), (II) or (IIa), $R^3$ is methyl.

In embodiments of compounds of Formula (I), (II) or (IIa), $R^2$ and $R^3$ are each methyl.

In embodiments of compounds of Formula (I), (II) or (IIa), $R^2$ and $R^3$ are each methyl, and $R^7$ is selected from the group consisting of hydrogen, methyl, ethyl, iso-propyl (1-methylethyl) and tert-butyl (1,1-dimethylethyl).

In embodiments of compounds of Formula (I), (II) or (IIa), $R^4$ is

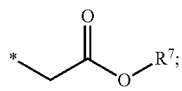

$R^7$ is hydrogen or $(C_1-C_6)$ alkyl, in particular hydrogen or $(C_1-C_4)$ alkyl, such as hydrogen, methyl, ethyl, iso-propyl and tert-butyl, more particularly methyl, ethyl, iso-propyl and tert-butyl;

$R^1$, $R^2$ and $R^3$ are each methyl.

In embodiments of compounds of Formula (I), (II) or (IIa), $R^4$ is $(C_1-C_6)$ alkyl, in particular $(C_1-C_4)$ alkyl; and $R^1$, $R^2$ and $R^3$ are each methyl.

In embodiments, compounds of Formula (I) are compounds of Formula (III), or a pharmaceutically acceptable salt thereof:

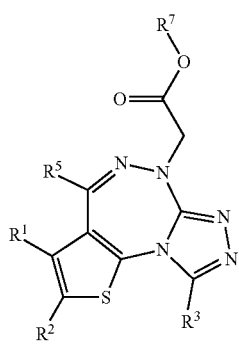

(III)

wherein $R^1$ and $R^2$ are each independently selected from the group consisting of a hydrogen, a halogen and $(C_1-C_6)$ alkyl;

$R^3$ is selected from the group consisting of $(C_1-C_6)$ alkyl, —OH and halogen;

$R^5$ is selected from the group consisting of an aryl, a heteroaryl, a benzodioxolane and a benzodioxane, wherein said aryl, heteroaryl, benzodioxolane or benzodioxane is optionally substituted with a halogen or a $(C_1-C_4)$ alkoxy group; and each $R^7$ is independently hydrogen or $(C_1-C_6)$ alkyl.

In embodiments, compounds of Formula (I) are compounds of Formula (IV), or a pharmaceutically acceptable salt thereof:

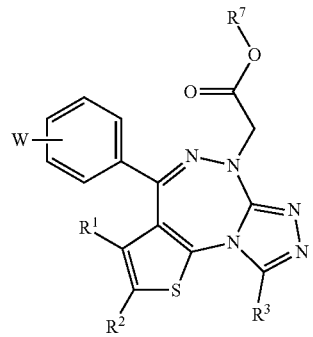

(IV)

wherein $R^1$ and $R^2$ are each independently selected from the group consisting of a hydrogen, a halogen and $(C_1-C_6)$ alkyl;

$R^3$ is selected from the group consisting of $(C_1-C_6)$ alkyl, —OH and halogen; each $R^7$ is independently hydrogen or $(C_1-C_6)$ alkyl; and W is a halogen (such as fluorine, chlorine, bromine or iodine), in particular W is chlorine.

In embodiments, compounds of Formula (I) are compounds of Formula (V), or a pharmaceutically acceptable salt thereof:

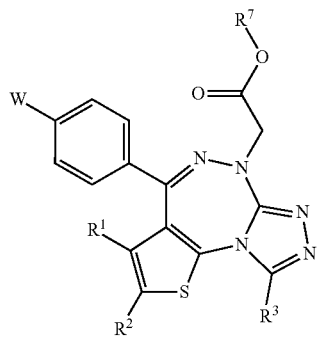

(V)

wherein $R^1$ and $R^2$ are each independently selected from the group consisting of a hydrogen, a halogen and $(C_1-C_6)$ alkyl;

$R^3$ is selected from the group consisting of $(C_1-C_6)$ alkyl, —OH and halogen; each $R^7$ is independently hydrogen or $(C_1-C_6)$ alkyl; and W is a halogen (such as fluorine, chlorine, bromine or iodine), in particular W is chlorine.

In embodiments of compounds of Formula (IV) and (V), $R^1$, $R^2$ and $R^3$ are each independently selected from $(C_1-C_6)$ alkyl, in particular $(C_1-C_3)$ alkyl.

In embodiments of compounds of Formula (IV) and (V), $R^7$ is selected from the group consisting of hydrogen or $(C_1-C_4)$ alkyl.

In embodiments of compounds of Formula (IV) and (V), $R^2$ and $R^3$ are each independently selected from $(C_1-C_3)$ alkyl, and $R^7$ is selected from the group consisting of hydrogen or $(C_1-C_4)$ alkyl.

Examples of compounds of Formulas (I), (II) and (IIa) include the structures set out below:

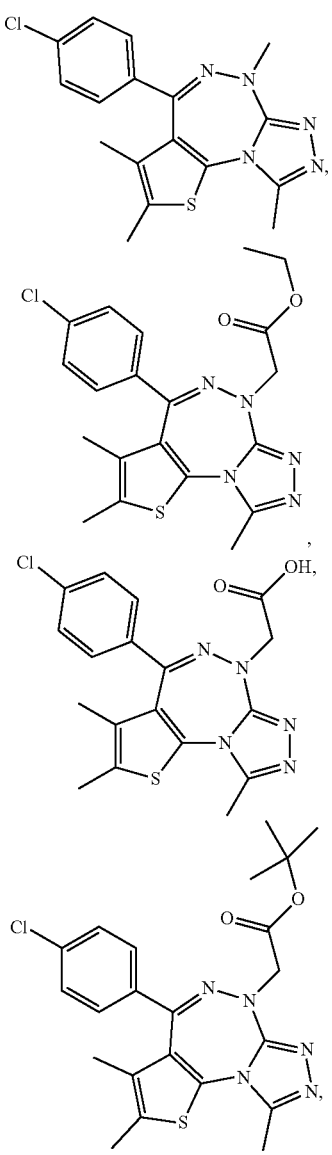

or a pharmaceutical salt thereof.

In a specific embodiment, the compound of Formula (I) is

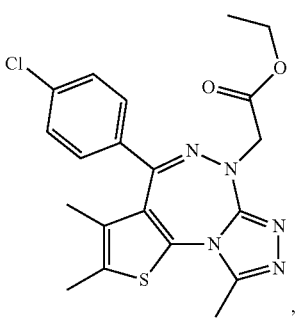 [SMILES: CCOC(=O)CN1N=C(c2ccc(Cl)cc2)c2c(sc(C)c2C)-n2c(C)nnc21]

or a pharmaceutical salt thereof.

As used herein, "alkyl" refers to straight and branched chain alkyl groups. The alkyl groups referred to herein are unsubtituted. The term "$(C_m$-$C_n)$" refers to a group with m to n carbon atoms. The term "$(C_1$-$C_6)$ alkyl" refers to a linear or branched hydrocarbon chain containing 1, 2, 3, 4, 5 or 6 carbon atoms. Examples of $C_{1-6}$ alkyls are such as methyl, ethyl, n-propyl, 1-methylethyl (iso-propyl), n-butyl, 1-methylpropyl (sec-butyl), 2-methylpropyl (iso-butyl), 1,1-dimethylethyl (tert-butyl), n-pentyl, dimethylpropyl (tert-pentyl), 2,2-dimethylpropyl (neo-pentyl), 3-methylbutyl (isopentyl), pentan-2-yl (sec-pentyl), pentan-3-yl, 3-methylbutan-2-yl or 2-methylbutyl. "$C_{1-4}$ alkyl" similarly refers to such groups containing up to 4 carbon atoms.

As used herein, the term "halo" or "halogen" refers to one of the halogens, group 17 of the periodic table. In particular, the term refers to fluorine, chlorine, bromine and iodine.

As used herein, the term "alkoxy" denotes —O-alkyl wherein alkyl is as defined above. $C_1$-$C_4$ alkoxy includes an alkyl having from 1 to 4 carbon atoms. Non-limiting examples of $C_1$-$C_4$ alkoxy are methoxy, ethoxy, n-propyloxy, iso-propyloxy, 2-methyl-1-propyloxy and 2-methyl-2-propyloxy.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

The heteroaryl group can be, for example, a 5- or 6-membered monocyclic ring. The ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

The term "optionally substituted" includes either groups, structures, or molecules that are substituted and those that are not substituted. Where a moiety is substituted, it may be substituted at any point on the moiety where chemically possible and consistent with atomic valency requirements.

A bond terminating in a "*" represents that the bond is connected to another atom that is not shown in the structure. A bond terminating inside a cyclic structure and not terminating at an atom of the ring structure represents that the bond may be connected to any of the atoms in the ring structure where allowed by valency.

As used herein, "compounds of the invention" includes compounds having formula I as set forth above, and pharmaceutically acceptable salts thereof. These may include the acid addition and base salts of the compounds. These may be acid addition and base salts of the compounds. Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. The pharmaceutically acceptable salts of the invention are preferably formed by addition of any acid known to be useful in the formation of pharmaceutical salts. Suitable acid salts are set forth, for example, in *Remington: The Science and Practice of Pharmacy*, 21$^{st}$ edition, Univ. of the Sciences in Philadelphia (2005). Preferred acids for salt formation are hydrochloric acid (HCl), hydrobromic acid (HBr), sulfuric acid, nitric acid, phosphoric acid, acetic acid, citric acid, fumaric acid, malic acid, succininc acid, tartaric acid, methanesulfonic acid, trifluoroacetic acid, and p-toluenesulfonic acid. Pharmaceutically acceptable salts of compounds of the invention may be prepared by for example, one or more of the following methods:

(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{17}$O, $^{18}$O, $^{13}$N, $^{15}$N, $^{18}$F, $^{36}$Cl, $^{123}$I, $^{125}$I, $^{32}$P, $^{35}$S and the like. The radionuclide that is used will depend on the specific application of that radio-labelled derivative. For example, for in vitro competition assays, $^3$H or $^{14}$C are often useful. For radio-imaging applications, $^{11}$C or $^{18}$F are often useful.

Isotopically-labelled compounds can generally be prepared by conventional techniques known to those skilled in the art or by processes analogous to those described using an appropriate isotopically-labelled reagent in place of the non-labelled reagent previously employed.

The selective replacement of hydrogen with deuterium in a compound may modulate the metabolism of the compound, the PK/PD properties of the compound and/or the toxicity of the compound. For example, deuteration may increase the half-life or reduce the clearance of the compound in-vivo. Deuteration may also inhibit the formation of toxic metabolites, thereby improving safety and tolerability. It is to be understood that the invention encompasses deuterated derivatives of compounds of formula (I). As used herein, the term deuterated derivative refers to compounds of the invention where in a particular position at least one hydrogen atom is replaced by deuterium. For example, one or more hydrogen atoms in a $C_{1-4}$-alkyl group may be replaced by deuterium to form a deuterated $C_{1-4}$-alkyl group, for example $CD_3$.

Certain compounds of the invention may exist in solvated as well as unsolvated forms such as, for example, hydrated forms. It is to be understood that the invention encompasses all such solvated forms or pharmaceutically acceptable salts thereof that possess BET inhibitory activity.

It is also to be understood that certain compounds of the invention may exhibit polymorphism, and that the invention encompasses all such forms that possess BET inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

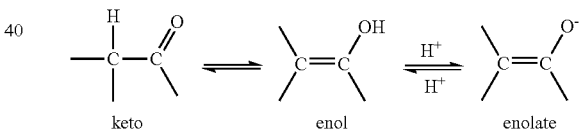

The in vivo effects of a compound of the invention may be exerted in part by one or more metabolites that are formed within the human or animal body after administration of a compound of the invention.

It is further to be understood that a suitable pharmaceutically-acceptable pro-drug of a compound of the formula (I) also forms an aspect of the present invention. Accordingly the compounds of the invention encompass pro-drug forms of the compounds and the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the invention as defined herein when made available by organic synthesis and when made available within the human or animal body by way of cleavage of a pro-drug thereof. Accordingly, the present invention includes those compounds of the formula (I) that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically-acceptable pro-drug of a compound of the invention is one that is based on reasonable medical judgement as being suitable for administration to the human or animal body without undesirable pharmacological activities and without undue toxicity.

Various forms of pro-drug have been described, for example in the following documents: Methods in Enzymology, Vol. 42, p. 309-396, edited by K. Widder, et al. (Academic Press, 1985); Design of Pro-drugs, edited by H. Bundgaard, (Elsevier, 1985); A Textbook of Drug Design and Development, edited by Krogsgaard-Larsen and H. Bundgaard, Chapter 5 "Design and Application of Pro-drugs", by H. Bundgaard p. 113-191 (1991); H. Bundgaard, Advanced Drug Delivery Reviews, 8, 1-38 (1992); H. Bundgaard, et al., Journal of Pharmaceutical Sciences, 77, 285 (1988); N. Kakeya, et al., Chem. Pharm. Bull., 32, 692 (1984); T. Higuchi and V. Stella, "Pro-Drugs as Novel Delivery Systems", A.C.S. Symposium Series, Volume 14; and E. Roche (editor), "Bioreversible Carriers in Drug Design", Pergamon Press, 1987.

As used herein, the terms treating" or "treatment" refers to any indicia of success in the treatment or amelioration of a disease, pathology or condition, including any objective or subjective parameter such as abatement; remission; diminishing of symptoms or making the pathology or condition more tolerable to the patient; slowing in the rate of degeneration or decline; making the final point of degeneration less debilitating; improving a patient's physical or mental well-being. The term "treating" and conjugations thereof, include prevention of a pathology, condition, or disease.

As used herein, a "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Pharmaceutical Compositions

The invention also provides pharmaceutical compositions comprising one or more compounds of the invention, in combination with one or more pharmaceutically acceptable carriers or excipients. Such excipients include, but are not limited to, fillers, binding agents, lubricants, preservatives, water, buffers, and disintegrants. The compositions may be in the form of solids or liquids compounded for oral administration (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration, such as solutions or suspensions suitable for parenteral administration (for example, a sterile aqueous or oily solution for intravenous, subcutaneous, intramuscular or intraperitoneal dosing or as a suppository for rectal dosing).

Pharmaceutically acceptable carriers and excipients are those compounds, solutions, substances or materials that can be used to produce formulations of the compounds of the present invention that are suitable for administered to a subject. In particular, the carriers and excipients of the present invention are those useful in preparing pharmaceutical compositions that are generally safe, non-toxic and neither biologically nor otherwise undesirable, and that may present pharmacologically favorable profiles, and includes carriers and excipient that are acceptable for veterinary use as well as human pharmaceutical use. Suitable pharmaceutically acceptable carriers and excipients are well known in art and can be determined by those of skill in the art as the clinical situation warrants. Suitable carriers and excipients are set forth, for example, in *Remington: The Science and Practice of Pharmacy,* $21^{st}$ edition, Univ. of the Sciences in Philadelphia (2005).

The skilled artisan will understand that diluents used for parenteral or oral administration are included within the scope of the terms carriers and excipients. Examples of suitable carriers and excipients include saline, buffered saline, dextrose, water, glycerol, ethanol, propylene glycol, polysorbate 80 (Tween™-80), poly(ethylene)glycol 300 and 400 (PEG 300 and 400), PEGylated castor oil (e.g. Cremophor™ EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholids, polymer matrices, biocompatible polymers, liposperes, vesicles, particles, and liposomes. Excipients, carriers, and diluents included in a formulation have different purposes depending, for example on the nature of the drug, the mode of administration, and the purpose for which the formulation is being applied. Examples of generally used excipients include, without limitation: stabilizing agents, solubilizing agents, emulsifiers, suspending or viscosity agents, inert diluents, fillers, disintegrating agents, binding agents, wetting agents, lubricating agents, antibacterials, antioxidants, chelating agents, sweeteners, perfuming agents, flavouring agents, coloring agents, administration aids, and combinations thereof.

The compositions may further contain common carriers and excipients such as cornstarch or gelatin, lactose, sucrose, microcrystalline cellulose, kaolin, mannitol, dicalcium phosphate, sodium chloride, alginic acid, croscarmellose sodium, and sodium starch glycolate.

Pharmaceutically acceptable excipients also include tonicity-adjusting agents that make the composition isotonic with blood; these are particularly desirable in injectable formulations. Suitable tonicity-adjusting agents include, but are not limited to, monosaccharides, disaccharides, trisaccharides, sugar alcohols, and mixtures thereof. Preferred agents are sucrose, dextrose, trehalose, mannitol, lactose, glycerol, and sorbitol.

An effective amount of a compound of the present invention for use in therapy of a condition is an amount sufficient to symptomatically relieve in a warm-blooded animal, particularly a human, the symptoms of the condition or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.1 mg to 0.5 g of active agent, such as from 0.5 to 100 mg of active agent, compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general lower doses will be administered when a parenteral route is employed. Thus, for example, for intravenous, subcutaneous, intramuscular or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. A compound of the invention may be administered orally, for example in the form of a tablet, or capsule dosage form. The daily dose administered orally may be, for example a total daily dose selected from 1 mg to 1000 mg, 5 mg to 1000 mg, 10 mg to 750 mg or 25 mg to 500 mg. Typically, unit dosage forms will contain about 0.5 mg to 0.5 g of a compound of this invention. In a particular embodiment the compound of the invention is administered parenterally, for example by intravenous administration. In another particular embodiment the compound of the invention is administered orally.

Synthesis

The compounds of the general formula (I) can be prepared by sequential chemical transformations using suitably selected protecting groups. The term "protecting group" refers to a chemical group that exhibits the following characteristics: 1) it reacts with a specific functionality to give a protected substrate that is stable to the projected reactions from which protection is desired; 2) it is selectively removable from the protected substrate to yield the desired functionality; and 3) it is removable in good yield by reagents compatible with the other functional group(s) present or generated in such projected reactions. Examples of suitable protecting groups can be found in Wuts and Greene (2007) *Greene's Protective Groups in Organic Synthesis*, 4th Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDMS), 9-fluorenylmethyl-oxycarbonyl (Fmoc), 6-nitroveratryloxy carbonyl (Nvoc), nitropiperonyl, pyrenylmethoxycarbonyl, benzyl, nitrobenzyl, dimethoxybenzyl, 5-bromo-7-nitroindolinyl, and the like. Preferred hydroxyl protecting groups include acetyl, benzoyl, benzyl, tetrahydropyranyl, TBDMS, methoxy or ethoxy methyl ether and the like. Preferred carboxyl protecting groups include, but are not limited to, methyl, ethyl, benzyl, TBDMS, 2,2,2-trichloroethyl, 2-(trimethylsilyl) ethyl, (2-(trimethylsilyl)ethoxy)methyl, phenyl and nitrophenyl esters, ethyl, methyl and phenyl thioesters, and the like.

Processes and intermediates used in the preparation of the compounds of the invention include, but are not limited to, the representative examples described below under "EXAMPLES". These intermediates are themselves embodiments of the invention.

Therapeutic Uses

The invention also provides a method of treating a patient afflicted with a neoplastic disease, such as cancer, which method comprises administering to the patient a therapeutically effective amount of a compound according to Formula (I), (II), (IIa) (III), (IV) or (V), including any of the specific compounds as disclosed herein.

Also provided is a method for treating an inflammatory disease, such as rheumatoid arthritis or acute respiratory distress syndrome, in a subject by administering to the subject a therapeutically effective amount of a compound according to Formula (I), (II), (IIa) (III), (IV) or (V), including any of the specific compounds as disclosed herein.

Also provided is a method for treating a fibrotic disease, such as non-alcoholic steatotic hepatitis, idiopathic pulmonary fibrosis, or advanced heart failure, in a subject by administering to the subject a therapeutically effective amount of a compound according to Formula (I), (II), (IIa) (III), (IV) or (V), including any of the specific compounds as disclosed herein.

In view of their potential effect on apoA1 production, subjects who may be treated with the compounds or compositions of the invention may also include patients experiencing or at high risk to experience acute coronary syndromes, stroke or peripheral artery disease.

Preferably, the compound or compounds as disclosed herein are administered in the form of a pharmaceutical composition as described above. Those skilled in the art will appreciate that suitable doses will vary with the particular compound, the route of administration, the condition to be treated, and the metabolic status of the patient. In general, daily doses in the range of 1 mg to 500 mg will be effective. Effective dosing levels can be determined by dose-ranging studies, which are routine and well within the ability of those skilled in the art. Dosing may be continuous (e.g., via an intravenous line), or unit doses can be administered orally one or more times daily, as needed to maintain an effective concentration in vivo.

Co-Administration

The methods of treatment according to the invention or the compound of the invention for use in the treatment of conditions as defined herein may be applied as a sole therapy or be a combination therapy with an additional active agent.

For example, where the condition is a inflammatory disease a compound of the invention may be used in combination with another anti-inflammatory agent. Examples of anti-inflammatory agents include, but are not limited to steroidal compounds e.g. glucocorticoid receptor agonists like dexamethasone or prednisolone, or non-steroidal compounds like indomethacin, naproxene, ibuprofene celecoxib, methotrexate, or TNF inhibitors like adalimumab or infliximab, or IL6 antagonists like tocilizumab.

For example, where the condition is a fibrotic disease a compound of the invention may be used in combination with another anti-fibrotic agent. Examples of anti-fibrotic agent agents include, but are not limited to inhibitors of collagen synthesis like .pirfenidone or tyrosine kinase inhibitors like nintedanib.

For example, where the condition is a neoplastic disease a compound of the invention may be used in combination with another anti-neoplastic agent. Examples of anti-neoplastic agents include, but are not limited to anthracycline compounds like doxorubicine, kinase inhibitors like trametinib, hedgehog pathway inhibitors like sonidegib, or blockers of Programmed Death Ligand 1 like durvalumab.

For example, the compounds of the invention may be coadministered with agents known to inhibit leukocytic and lymphocytic proliferation such as daunorubicin, cytarabide, platinum salts, or bleomycin.

The terms "co-administration" and "co-administered" and the like, when used herein, are meant to refer to use of the compounds of the invention and any of the agents inhibiting the. The combined use may be performed simultaneously or sequentially in any order. With the invention, the compounds may be combined in one pharmaceutical composition, or they may be placed in separate compositions and administered to the patient at different times within the same treatment.

The following examples are presented by way of example and are intended to illustrate and explain the invention in detail. The scope of the invention is not limited to the examples presented.

EXAMPLES

Abbreviations:
AcOH Acetic acid
Boc tert.-Butyloxycarbonyl
DCM Dichloromethane
DIEA Diisopropylethylamine
DMEM Dulbecco's Modified Eagle Medium
DMF N,N-Dimethylformamide
EDCI 1-ethyl-3-(3-dimethylaminopropyl) carbodiimide hydrochloride
ELISA Enzyme-linked immunosorbent assay
EtOH ethanol
FCS fetal calf serum
HPLC high performance liquid chromatography
IPA 2-propanol
LPS Lipopolysaccharide
MeOH methanol
MS mass spectroscopy
NaOAc Sodium acetate
NMR Nuclear Magnetic Resonance Spectroscopy
PEG Poly(ethylene glycol)
sat. saturated
tBu tert-Butyl
TEA Triethylamine
THF tetrahydrofuran
TLC thin layer chromatography
TsOH p-Toluenesulfonic acid The title compounds of the Examples 1-4 have been named using ChemDraw® Professional, version 17.1.0.105 (19).

Example 1

4-(4-chlorophenyl)-2,3,6,9-tetramethyl-6H-thieno[2,3-e][1,2,4]triazolo[3,4-c][1,2,4]triazepine ("Compound 38")

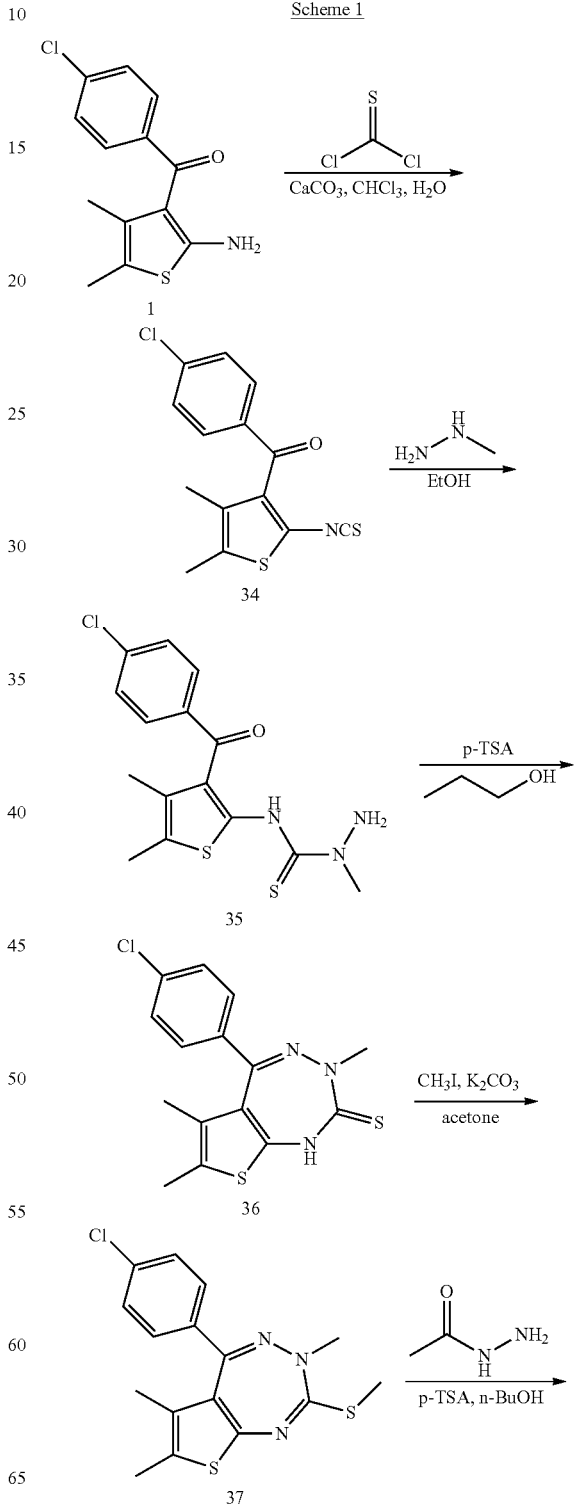

Scheme 1

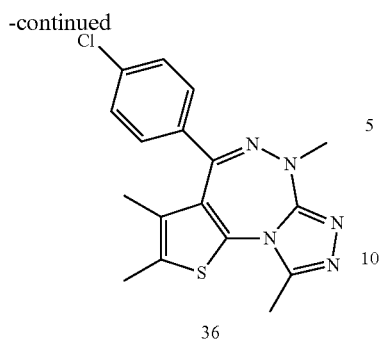

3-[(4-chlorophenyl)carbonyl]-4,5-dimethylthiophen-2-amine (1)

Into a 2-L 3-necked round-bottom flask were placed 3-(4-chlorophenyl)-3-oxopropanenitrile (60 g, 334.07 mmol, 1.00 equiv), ethanol (600 mL), butan-2-one (26.5 g, 367.52 mmol, 1.10 equiv), sulfur (12 g, 374.3 mmoles of elemental sulfur), and morpholine (32.3 g, 370.75 mmol, 1.11 equiv). The solution was stirred overnight at 85° C. and then concentrated under vacuum. The resulting solution was extracted with 3×400 mL of ethyl acetate and the organic layers were combined. The mixture was washed with 2×300 mL of H₂O, 1×200 mL of saturated sodium chloride (aq), dried over anhydrous sodium sulfate and concentrated under vacuum. This resulted in 45 g (169.33 mmoles, 51%) of 3-[(4-chlorophenyl)carbonyl]-4,5-dimethylthiophen-2-amine (1) as a yellow solid. ¹H-NMR (CDCl₃, 400 MHz): δ 7.48-7.46 (d, J=8.4 Hz, 2H), 7.40-7.38 (d, J=8.4 Hz, 2H), 2.14 (s, 3H), 1.56 (s, 3H).

(4-Chlorophenyl)(2-isothiocyanato-4,5-dimethylthiophen-3-yl)methanone (34)

Into a 250-mL 3-necked round-bottom flask was placed chloroform/H₂O=½ (60 mL), CaCO₃ (7.5 g), and thiophosgene (36.5 mL). This was followed by the addition of a solution of 1 (10 g, 37.63 mmol, 1.00 equiv) in chloroform (70 mL) dropwise with stirring at 0° C. The resulting solution was stirred for 3 h at 0° C. The reaction was then quenched by the addition of 30 mL of water. The mixture was washed with 4×200 mL of H₂O, dried over anhydrous sodium sulfate and concentrated under vacuum. This resulted in 13 g (112%) of 34 as yellow oil which was used in the next step without further purification.

1-Amino-1-methyl-3-(3-(4-chlorobenzoyl)-4,5-dimethylthiophen-2-yl)thiourea (35)

Into a 250-mL 3-necked round-bottom flask was placed 34 (13 g, max 37.63 mmol, 1.00 equiv) and ethanol (100 mL). This was followed by the addition of methylhydrazine (4.875 g, 105.81 mmol, 1.00 equiv) dropwise with stirring at 0° C. The resulting solution was stirred for 3 h at 0° C. The solids were collected by filtration and dried in an oven under reduced pressure. This resulted in 4.6 g (35% over two steps, 13.0 mmoles) of 35 as a yellow solid. ¹H-NMR (CDCl₃, 300 MHz): δ 7.56-7.54 (d, J=8.8 Hz, 2H), 7.40-7.37 (d, J=6.9 Hz, 2H), 3.76-3.69 (m, 3H), 2.26 (s, 3H), 1.67 (s, 3H).

5-(4-Chlorophenyl)-3,6,7-trimethyl-1H-thieno[2,3-e][1,2,4]triazepine-2(3H)-thione (36)

Into a 100-mL round-bottom flask was placed 35 (4.6 g, 13.00 mmol, 1.00 equiv), propan-1-ol (50 mL), and TsOH (224 mg, 1.30 mmol, 0.10 equiv). The resulting solution was stirred for 3 h at 100° C. The reaction mixture was cooled to room temperature and the solids were collected by filtration. The solid was dried in an oven under reduced pressure. This resulted in 2.2 g (50%, 6.55 mmoles) of 36 as a brown solid. MS (ES, m/z): 336 [M+H]⁺. ¹H-NMR (CDCl₃, 400 MHz): δ 10.96 (s, 1H), 7.56-7.54 (d, J=8.4 Hz, 2H), 7.44-7.42 (d, J=8.8 Hz, 2H), 3.34 (s, 3H), 2.23 (s, 3H), 1.49 (s, 3H).

5-(4-Chlorophenyl)-3,6,7-trimethyl-2-(methylthio)-3H-thieno[2,3-e][1,2,4]triazepine (37)

Into a 100-mL round-bottom flask was placed 36 (700 mg, 2.08 mmol, 1.00 equiv), propan-2-one (30 mL), potassium carbonate (2.88 g, 20.84 mmol, 10.00 equiv), and iodomethane (0.2 mL). The resulting solution was stirred for 3 h at 50° C. The reaction was then quenched by the addition of 50 mL of water. The solution was extracted with 3×200 mL of dichloromethane and the organic layers were combined. The mixture was washed with 3×200 mL of H₂O, 1×200 mL of sodium chloride (aq), dried over anhydrous sodium sulfate and concentrated under vacuum. This resulted in 750 mg (quant., 2.14 mmoles) of crude 37 as a yellow solid. ¹H-NMR (CDCl₃, 300 MHz): δ 7.40-7.32 (m, 4H), 3.26 (s, 3H), 2.50 (s, 3H), 2.24 (s, 3H), 1.52 (s, 3H).

2,3,6,9-Tetramethyl-4-(4-chlorophenyl)-6H-thieno[3,2-f]-triazolo[4,3-a][1,3,4]triazepine (38)

Into a 100-mL round-bottom flask was placed 37 (700 mg, 2.00 mmol, 1.00 equiv), n-BuOH (25 mL), p-TSA (34.4 mg, 0.10 equiv), and acetohydrazide (148 mg, 2.00 mmol, 1.00 equiv). The resulting solution was stirred overnight at 100° C. The reaction was then quenched by the addition of 4 mL of water. The solution was extracted with 3×200 mL of dichloromethane and the combined organic layers were dried over anhydrous sodium sulfate and concentrated under vacuum. The residue was applied onto a silica gel column with ethyl acetate/petroleum ether (1/1). This resulted in 105.6 mg (15%) of 38 as a light yellow solid. MS (ES, m/z): 358 [M+H]⁺. ¹H-NMR (CDCl₃, 300 MHz): δ 7.45-7.42 (d, J=8.7 Hz, 2H), 7.37-7.34 (d, J=8.7 Hz, 2H), 3.45 (s, 3H), 2.65 (s, 3H), 2.37 (s, 3H), 1.61 (s, 3H).

Examples 2-4

Scheme 2

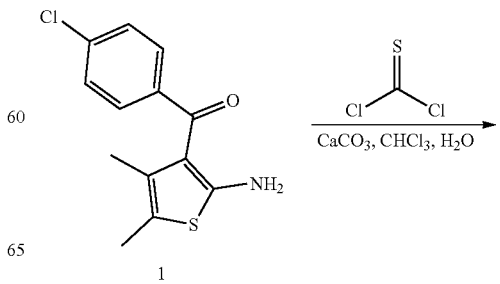

-continued

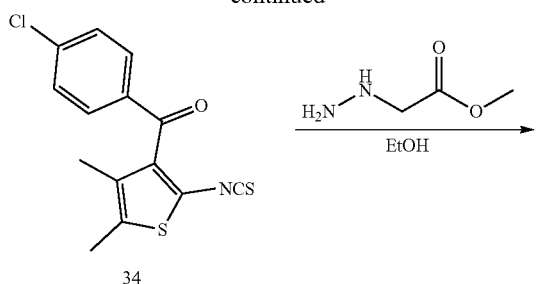

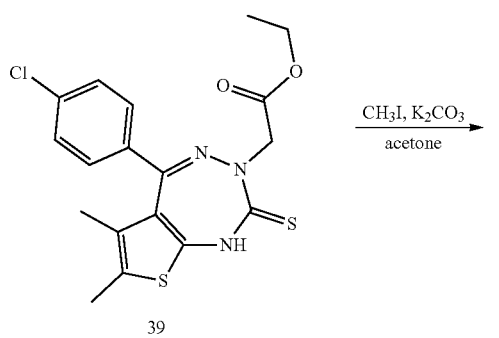

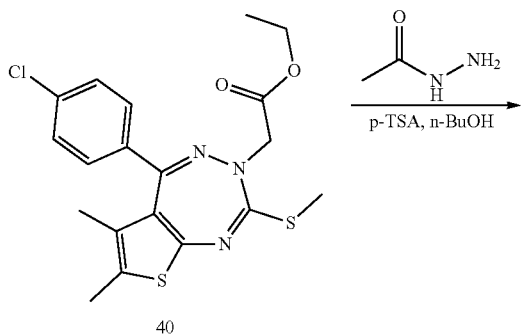

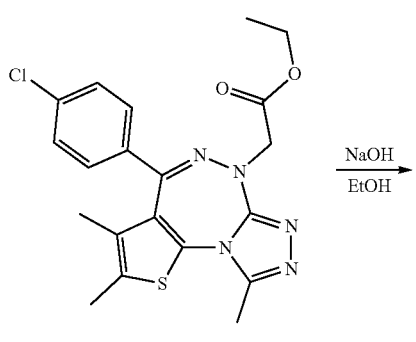

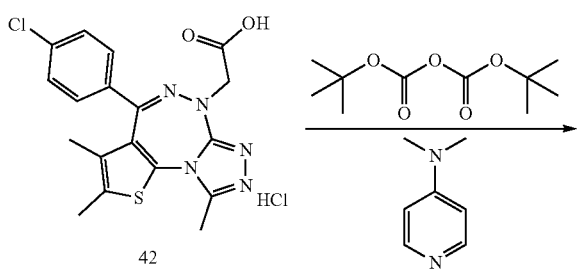

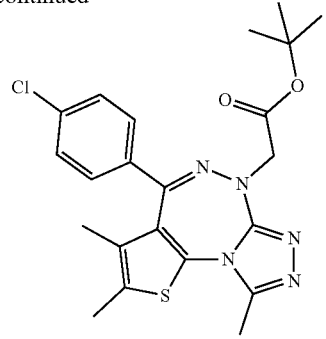

(4-chlorophenyl)(2-isothiocyanato-4,5-dimethylthiophen-3-yl)methanone (34)

Into a 250-mL round-bottom flask was placed a solution of 1 (10 g, 37.63 mmol, 1.00 equiv) in 90 mL chloroform, CaCO₃ (7.5 g, 1.90 equiv),), water (40 mL), and chloromethanecarbothioyl chloride (22 g, 191.33 mmol, 4.70 equiv). The resulting solution was stirred for 2 h at 0° C. The mixture was washed with 4×100 mL of brine and then concentrated. The residue was applied onto a silica gel column with ethyl acetate/petroleum ether (1:20). This resulted in 8.2 g (71%) of (4-chlorophenyl)(2-isothiocyanato-4,5-dimethylthiophen-3-yl)methanone as brown oil.

Ethyl 2-[5-(4-chlorophenyl)-6,7-dimethyl-2-sulfanylidene-1H,2H,3H-thieno[2,3-e][1,2,4]triazepin-3-yl]acetate (39)

Into a 250-mL round-bottom flask was placed a solution of 34, (4-chlorophenyl)(2-isothiocyanato-4,5-dimethylthiophen-3-yl)methanone, (6 g, 19.49 mmol, 1.00 equiv) in tert-butanol (40 mL), ethyl 2-hydrazinylacetate hydrochloride (3 g, 19.41 mmol, 1.00 equiv). The solution was stirred for 1 h at 90° C. The solution was diluted with 100 mL of EA and the resulting mixture was washed with 3×30 mL of brine. The residue was applied onto a silica gel column with ethyl acetate/petroleum ether (1:5). This resulted in 5.2 g (65%) of ethyl 2-[5-(4-chlorophenyl)-6,7-dimethyl-2-sulfanylidene-1H,2H,3H-thieno[2,3-e][1,2,4]triazepin-3-yl]acetate, 39, as a yellow solid.

Ethyl 2-[5-(4-chlorophenyl)-6,7-dimethyl-2-(methylsulfanyl)-3H-thieno[2,3-e][1,2,4]triazepin-3-yl]acetate (40)

Into a 100-mL round-bottom flask was placed 39, ethyl 2-[5-(4-chlorophenyl)-6,7-dimethyl-2-sulfanylidene-1H,2H,3H-thieno[2,3-e][1,2,4]triazepin- 3-yl]acetate, (5.2 g, 12.75 mmol, 1.00 equiv), CH₃I (3.6 g, 25.36 mmol, 2.00 equiv), potassium carbonate (5.6 g, 40.52 mmol, 3.00 equiv), and acetone (50 mL). The resulting solution was stirred for 6 h at room temperature. The solution was diluted with 100 mL of EA and the mixture was washed with 3×40 mL of brine. The residue was applied onto a silica gel column with ethyl acetate/petroleum ether (1:15). This resulted in 5.4 g (100%) of ethyl 2-[5-(4-chlorophenyl)-6,7-dimethyl-2-(methylsulfanyl)-3H-thieno[2,3-e][1,2,4]triazepin-3-yl]acetate, 40, as a yellow solid.

Example 2

Ethyl 2-(4-(4-chlorophenyl)-2,3,9-trimethyl-6H-thieno[2,3-e][1,2,4]triazolo[3,4-c][1,2,4]triazepin-6-yl)acetate ("Compound 41")

Into a 100-mL round-bottom flask was placed a solution of 40, ethyl 2-[5-(4-chlorophenyl)-6,7-dimethyl-2-(methylsulfanyl)-3H-thieno[2,3-e][1,2,4]triazepin-3-yl]acetate, (600 mg, 1.42 mmol, 1.00 equiv) in i-propanol (15 mL), p-TSA (26 mg, 0.10 equiv), and acetohydrazide (200 mg, 2.70 mmol, 2.00 equiv). The resulting solution was stirred for 5 h at 90° C. The mixture was concentrated and the residue was applied onto a silica gel column with ethyl acetate/petroleum ether (3:2). This resulted in 0.21 g (34%) of ethyl 2-[7-(4-chlorophenyl)-4,5,13-trimethyl-3-thia-1,8,9,11,12-pentaazatricyclo[8.3.0.0^[2,6]]trideca-2(6),4,7,10,12-pentaen-9-yl]acetate, 41, as a yellow solid. LCMS (33, ESI): RT=5.29 min, m/z=429.95 [M+H]$^+$. $^1$H-NMR (300 MHz, CDCl$_3$): δ 7.33-7.40 (m, 4H), 4.60 (d, br, 2H), 4.24 (m, 2H), 2.63 (s, 3H), 2.36 (s, 3H), 1.60 (s, 3H), 1.02 (t, 3H).

Example 3

2-(4-(4-chlorophenyl)-2,3,9-trimethyl-6H-thieno[2,3-e][1,2,4]triazolo[3,4-c][1,2,4]triazepin-6-yl)acetic acid hydrochloride ("Compound 42")

Into a 50-mL round-bottom flask was placed 41, ethyl 2-[7-(4-chlorophenyl)-4,5,13-trimethyl-3-thia-1,8,9,11,12-pentaazatricyclo[8.3.0.0^[2,6]]trideca-2(6),4,7,10,12-pentaen-9-yl]acetate, (3 g, 6.98 mmol, 1.00 equiv), EtOH (20 mL), and hydrogen chloride (12N) (10 mL). The resulting solution was stirred for 5 h at 50° C. and then concentrated under vacuum. This resulted in 2.6 g (85%) of 2-[7-(4-chlorophenyl)-4,5,13-trimethyl-3-thia-1,8,9,11,12-pentaazatricyclo[8.3.0.0^[2,6]]trideca-2(6),4,7,10,12-pentaen-9-yl]acetic acid hydrochloride, 42, as a yellow solid. LCMS (33, ESI): RT=1.87 min, m/z=401.85 [M+H]$^+$. $^1$H-NMR (300 MHz, CDCl$_3$): δ 7.41-7.48 (m, 4H), 4.50 (d, br, 2H), 2.65 (s, 3H), 2.41 (s, 3H), 1.49 (s, 3H).

Example 4 tert-butyl 2-(4-(4-chlorophenyl)-2,3,9-trimethyl-6H-thieno[2,3-e][1,2,4]triazolo[3,4-c][1,2,4]triazepin-6-yl)acetate ("Compound 43")

Into a 100-mL round-bottom flask was placed a solution of 42, 2-[7-(4-chlorophenyl)-4,5,13-trimethyl-3-thia-1,8,9,11,12-pentaazatricyclo[8.3.0.0^[2,6]]trideca-2(6),4,7,10,12-pentaen-9-yl]acetic acid hydrochloride, (2.2 g, 5.02 mmol, 1.00 equiv) in tert-butanol (50 mL), N,N-dimethylpyridin-4-amine (600 mg, 4.91 mmol, 1.00 equiv), and di-tert-butyl dicarbonate (2.3 g, 10.54 mmol, 2.00 equiv). The resulting solution was stirred for 10 h at 50° C. The mixture was cooled and the residue was applied onto a silica gel column with ethyl acetate/petroleum ether (1:1). The crude product was purified by prep-HPLC with the following conditions: Column, Xbridge Shield RP 18, 5 um, 19*150 mm; mobile phase, water with 50 mmol NH$_4$HCO$_3$ and CH$_3$CN (10.0% CH$_3$CN up to 28.0% in 2 min, up to 46.0% in 10 min, up to 100.0% in 1 min, down to 10.0% in 1 min); Detector, UV 254 nm. This resulted in 0.8 g (35%) of tert-butyl 2-[7-(4-chlorophenyl)-4,5,13-trimethyl-3-thia-1,8,9,11,12-pentaazatricyclo[8.3.0.0^[2,6]]trideca-2(6),4,7,10,12-entaen-9-yl]acetate, 43, as a yellow solid. LCMS (33, ESI): RT=7.60 min, m/z=458.0 [M+H]$^+$. $^1$H-NMR (300 MHz, CDCl$_3$): δ 7.31-7.40 (m, 4H), 4.50 (d, br, 2H), 2.64 (s, 3H), 2.35 (s, 3H), 1.60 (s, 3H), 1.49 (s, 9H).

Example 5

Bromodomain 4 Inhibition

AlphaScreen assays were performed as described by Philpott et al *Mol Biosyst*. 2011; 7:2899-2908. A 12-point 1:2 serial dilution of the ligands was prepared to provide a 0-250 μM final assay concentration range. YSGRGK(Ac)GGK(Ac)GLGK(Ac)GGAK(Ac)RHRK (Biotin) peptide was used in the assays. Buffer conditions used in all experiments were 25 mM HEPES, pH 7.4, 100 mM NaCl, 0.1% BSA, supplemented with 0.05% CHAPS. (+)JQ-1 was used as reference compound.

TABLE 1

Potency of thienotriazolotriazepines as inhibitor of BRD4, expressed as IC-50 (nM)

| Compound | IC-50 (nM) |
| --- | --- |
| 38 | 150 |
| 41 | 11 |
| 42 | 290 |
| 43 | 100 |
| (+)JQ1 | 280 |

The data in Table 1 shows similar or improved potency of BRD4 inhibition by the thienotriazolotriazepines as disclosed herein as compared to the reference (+) JQ-1 compound.

Example 6

Inhibition of Proliferation of Leukemia and Multiple Lyeloma Cell Lines

"Compound 38" (Example 1) was diluted in 100% DMSO to generate a 1000-fold concentrated stock solution with a concentration of 300 μM. A semi-log dilution was performed in 100% DMSO. Cells were cultured in DMEM containing 10% FCS and Penicillin/Streptomycin. For the assays, cells were seeded in 150 μL medium on a 96-well cell culture plate and incubated at 37° C. overnight before the compound was added. "Compound 38" was prepared as predilution in medium which was 16-fold concentrated to the final assay concentration. A day after cell seeding, 10 μL of prediluted compound was added to the cells (1:16 dilution). Treatment of cells with 0.1% DMSO and Staurosporine (1.0E-05 M) served as High control (100% viability) and Low control (0% viability), respectively Measurement of the impact of "Compound 38" on cell viability was performed as follows: 2.500 cells/well were seeded in the inner wells of 96-well-plates in 150 μL complete medium. A day after cell seeding, the test compound was added to the medium to reach the final concentration and incubated for 72 h at 37° C. at 5% CO2 in air dependent on the medium. Subsequently 15 μL Alamar Blue reagent was added and fluorescence at 590 nm was measured after 3-5 h incubation at 37° C., 5% CO2 using a fluorometer.

Raw data were converted into percent cell viability relative to the high control (0.1% DMSO) and low control (1E-05M Staurosporine), which were set to 100% and 0%, respectively. IC50 calculation was performed using Graph- Pad Prism software with a variable slope sigmoidal response fitting model using 0% cell growth as bottom constraint or no constraint (as indicated) and 100% cell growth as top constraint.

"Compound 38" was compared with the reference compound (+)JQ1. The results presented in Table 2 show clear inhibition of cell growth by "Compound 38" in two different acute myeloma and three different multiple myeloma cell lines, although somewhat less potent than the reference compound.

TABLE 2

Inhibition of cell growth by "Compound 38" and by (+)JQ1. (Values represent IC50 as nM)

| Cancer type | Cell line | 38 | (+)JQ1 |
|---|---|---|---|
| AML | HL-60 | 810 | 260 |
| AML | KG1 | 810 | 350 |
| Multiple myeloma | KMS-12-BM | 270 | 120 |
| Multiple myeloma | LP-1 | 360 | 120 |
| Multiple myeloma | OPM-2 | 260 | 95 |

Example 7

Anti Inflammatory Effects

BET inhibitors were added (from 10 mM DMSO solutions) to whole human blood (anti-coagulated with heparin) during incubation for 24 h at 37° C. in the presence of 10 ng/ml Lipopolysaccharide (LPS). Final DMSO concentration was below 0.01%. Cytokines production with 0.01% DMSO alone in the absence of LPS were below detection level.

Figure 1B:
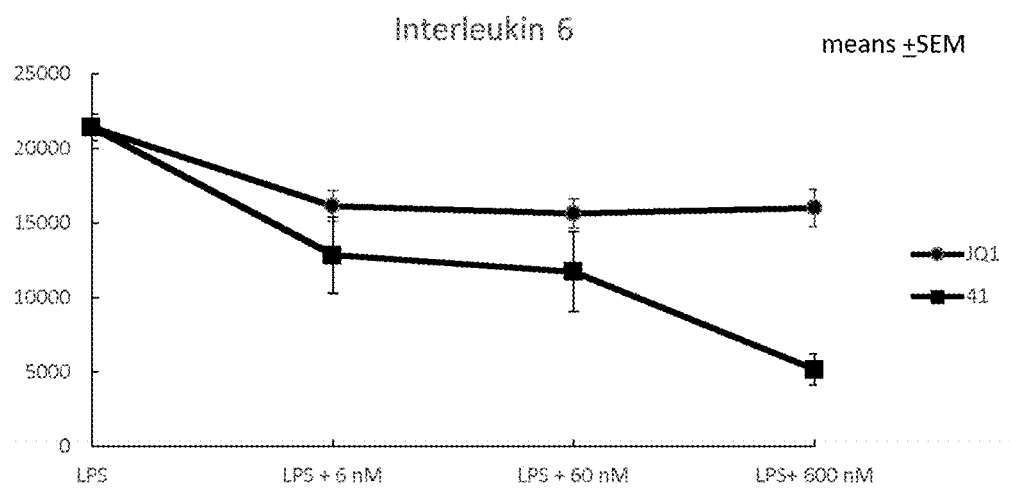
Figure 1C:
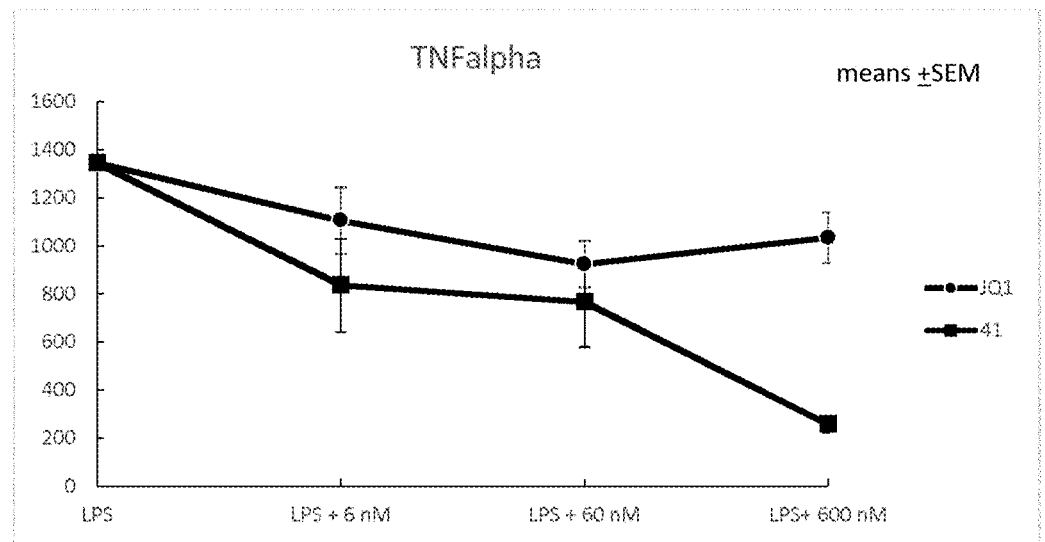

Production of inflammatory cytokines Interleukin 1beta (IL-1beta), Interleukin 6 (IL6) and TNF-alpha was inhibited by "Compound 41" (Example 2) with IC50s of between 6 and 60 nM respectively. Remarkably, at 600 nM concentration inhibition by "Compound 41" exceeded 80% whereas inhibition by compound (+)-JQ1 was only about 30% as shown in FIG. 1.

Example 8

Production of the Chemokine CC12 by Cultured Human Astrocytes

Figure 2:
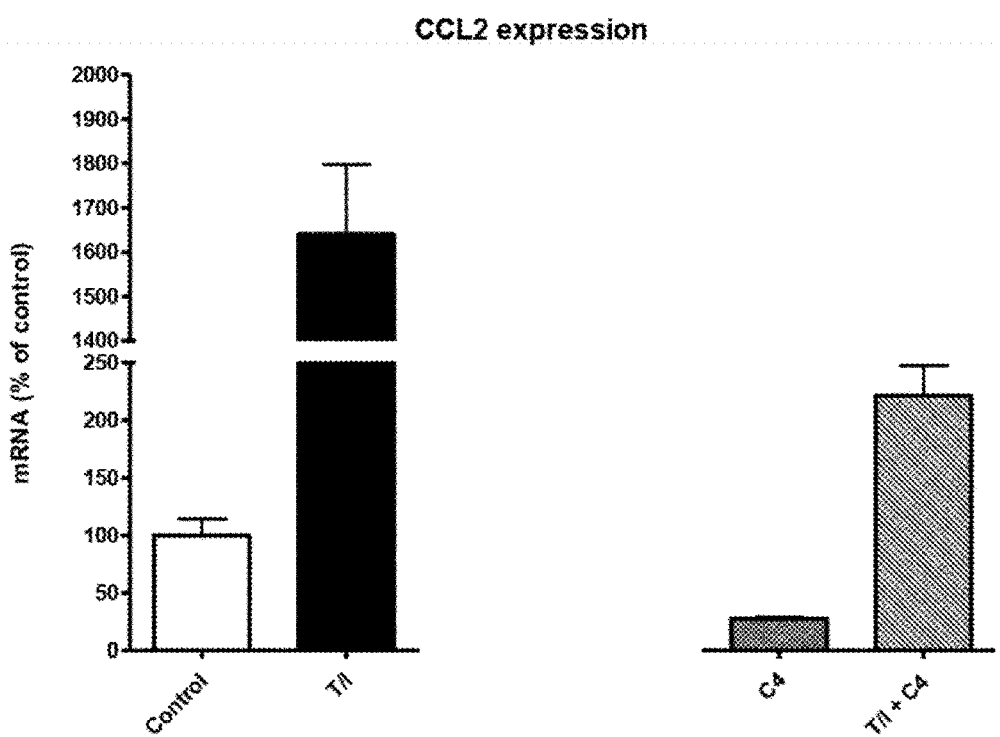
FIG. 2 illustrates the effect of "Compound 38" (also called "C4"; Example 1) on expression of Chemokine CCL2 by human astrocytes, stimulated by TNFalpha and Interferon-alpha (T/I).

CCL2 mRNA content of control astrocytes, astrocytes incubated with 10 ug/ml Tumor Necrosis Factor alpha (TNFalpha) and 10 ug/ml Interferon alpha (IFNalpha) (T/I), astrocytes treated with 250 nM of "Compound 38" (referred to as "C4" in FIG. 2) and astrocytes which are pretreated with "Compound 38" (C4) for 1 hour before stimulation with T/I. Incubation period 24 h. Details on astrocyte culture and quantification of CCL2 mRNA are provided in Mizee et al. Acta Neuropathol (2014) 128:691-703. FIG. 2 shows that CCL2 expression is strongly stimulated by addition of TNFa/Interferon. Co-addition of 250 nM of "Compound 38" decreased CCL2 production by 80% both in the absence and presence of TNFalpha/Interferon as shown in FIG. 2.

Example 9

Anti-Fibrotic Effects

Methods of culturing LX2 cells and measurements of Collagen1A1 and alphaActin1 mRNA contents are provided in Ding et al, Proc Natl Acad Sci USA 2015, 112:15713-15718

Figure 3A:
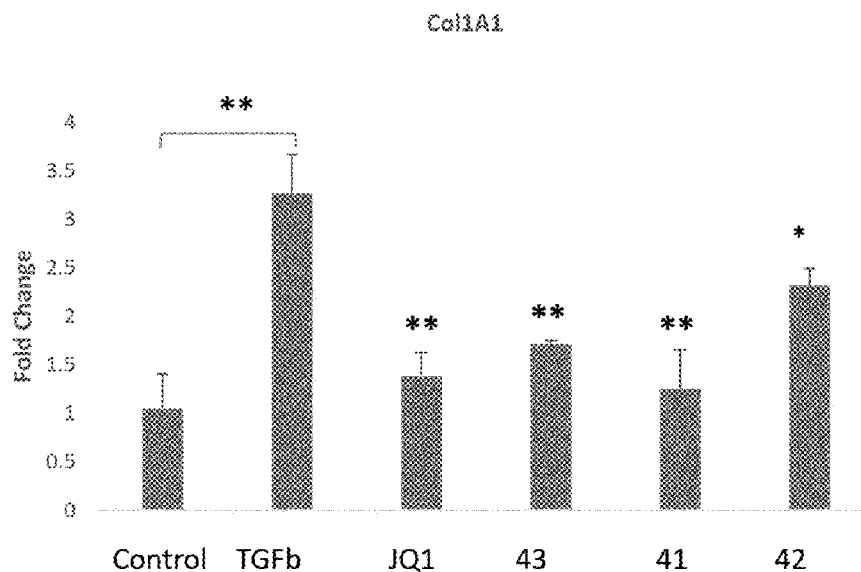
FIGS. 3A and 3B illustrate the effects of "Compound 41" (Example 2), "Compound 42" (Example 3) and "Compound 43" (Example 4) and of reference compound (+)JQ1 on the expression of collagen 1A1 (FIG. 3A) or alphaActin 1 (FIG. 3B) by LX2 cells (liver stellate cell line) treated with TGFbeta.
Figure 3B:
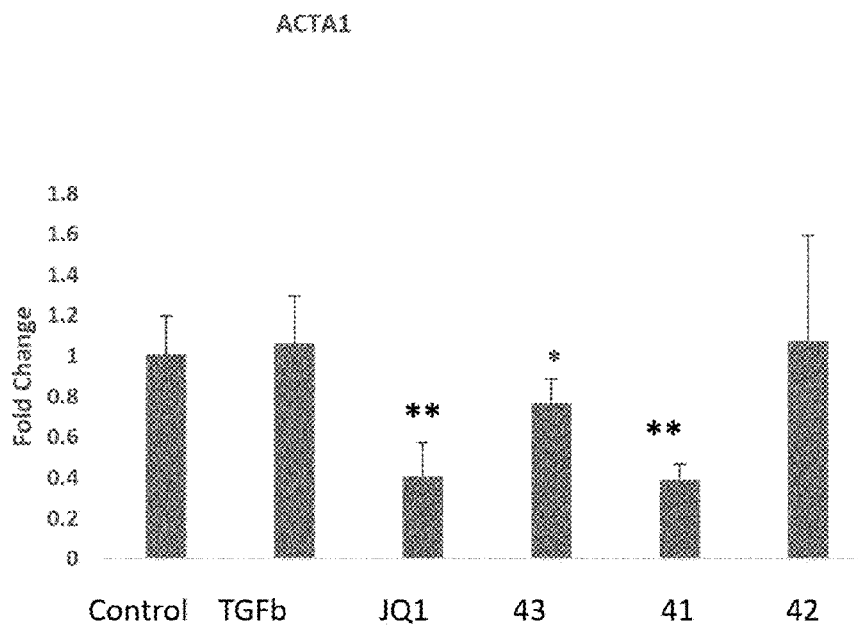

As shown in FIG. 3, incubation of LX2 cells (liver stellate cell line) with TGFbeta strongly stimulates production of collagen1A1 and alpha-Actin1 and alpha-Actin2. In this condition, collagen1A1 and alphaActin1 production were reduced to an equal extent by 500 nM "Compound 41" and (+)JQ1, whereas "Compound 42" and "Compound 43" showed less inhibition.

It is understood that the examples and embodiments described herein are for illustrative purposes only and that various modifications or changes in light thereof will be suggested to persons skilled in the art and are to be included within the scope of the appended claims.

All documents, including but not limited to publications, patents, patent applications, books, manuals, articles, papers, abstracts, and posters, and other materials referenced herein are expressly incorporated herein by reference in their entireties.

What is claimed is:

1. A method of treating a disease selected from the group consisting of a blood cancer, rheumatoid arthritis, acute respiratory distress syndrome, non-alcoholic steatotic hepatitis, idiopathic pulmonary fibrosis, and cardiac fibrosis in advanced heart failure, in a subject in need thereof, the method comprising administering to the subject a therapeutically effective amount of a compound of having the following formula (I),

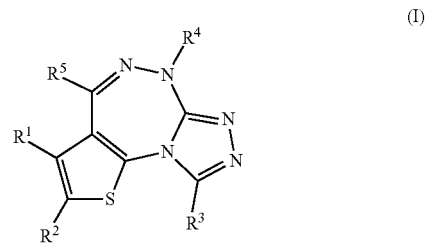

or a pharmaceutically acceptable salt thereof, wherein:
$R^1$ and $R^2$ are each independently selected from the group consisting of hydrogen, halogen, and ($C_1$-$C_6$) alkyl;
$R^3$ is selected from the group consisting of ($C_1$-$C_6$) alkyl, —OH, and halogen;
$R^4$ is selected from the group consisting of ($C_1$-$C_4$) alkyl and

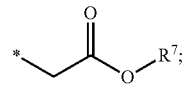

$R^5$ is selected from the group consisting of an aryl, a heteroaryl, a benzodioxolane and a benzodioxane, wherein said aryl, heteroaryl, benzodioxolane or benzodioxane is optionally substituted with a halogen or a $(C_1-C_4)$alkoxy group;
$R^7$ is $(C_1-C_6)$ alkyl.

2. The method according to claim 1, wherein $R^4$ is $(C_1-C_4)$ alkyl.

3. The method according to claim 1, wherein $R^4$ is

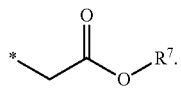

4. The method according to claim 1, wherein $R^7$ is $(C_1-C_4)$ alkyl.

5. The method according to claim 1, wherein $R^4$ is

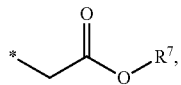

and $R^7$ is ethyl.

6. The method according to claim 1, wherein $R^5$ is selected from the group of

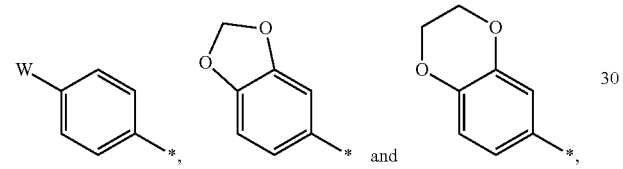

wherein W is a halogen.

7. The method according to claim 1, wherein $R^5$ is phenyl substituted with a halogen.

8. The method according to claim 1, wherein $R^5$ is phenyl substituted with chlorine.

9. The method according to claim 1, wherein the compound of Formula (I) is a compound of Formula (IIa):

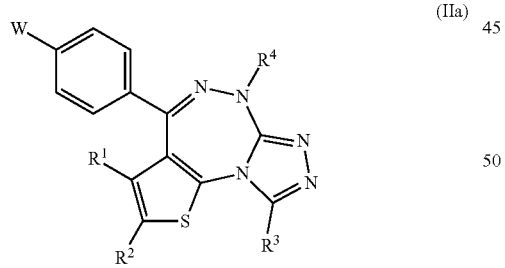

(IIa)

wherein W is a halogen,
or a pharmaceutically acceptable salt thereof.

10. The method according to claim 9, wherein W is chloro.

11. The method according to claim 1, wherein $R^1$ and $R^2$ are each independently selected from $(C_1-C_3)$ alkyl.

12. The method according to claim 1, wherein $R^1$ and $R^2$ are methyl.

13. The method according to claim 1, wherein $R^3$ is $(C_1-C_3)$ alkyl.

14. The method according to claim 1, wherein $R^3$ is methyl.

15. The method according to claim 1, wherein $R^4$ is

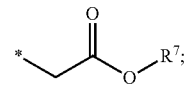

$R^7$ is ethyl; and
$R^1$, $R^2$ and $R^3$ are each methyl.

16. The method according to claim 1, wherein the compound is selected from the group consisting of

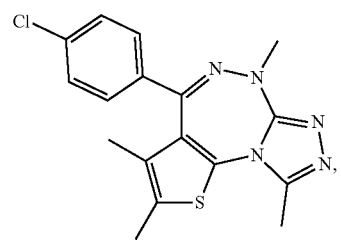

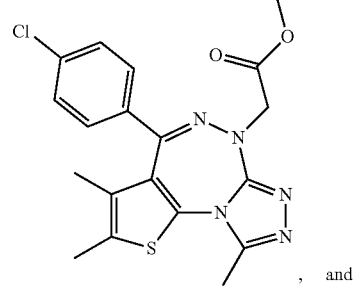

, and

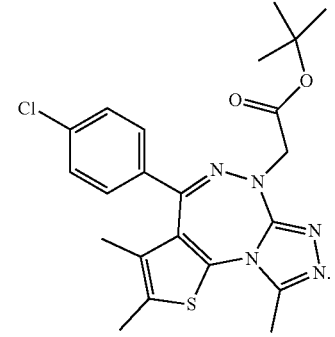

17. The method according to claim 1, wherein the compound is

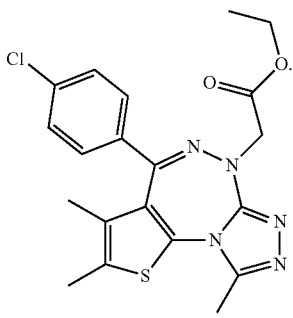 [SMILES: CCOC(=O)CN1N=C(c2ccc(Cl)cc2)c2c(sc(C)c2C)-n2c(C)nnc21]

18. The method of claim 1, wherein the subject has, or is at risk of developing, one or more of an acute coronary syndrome, stroke and/or peripheral artery disease.

19. The method of claim 1, wherein the compound is administered to the subject in combination with an agent selected from an anti-inflammatory agent, an anti-fibrotic agent, an anti-neoplastic agent and an agent which inhibits leukocytic or lymphocytic proliferation, wherein the anti-inflammatory agent is selected from dexamethasone, prednisolone, indomethacin, naproxene, ibuprofene celecoxib, methotrexate, adalimumab, infliximab and tocilizumab;

the anti-fibrotic agent is selected from pirfenidone and nintedanib;

the anti-neoplastic agent is selected from doxorubicine, trametinib, sonidegib and durvalumab; and the agent which inhibits leukocytic or lymphocytic proliferation is selected from daunorubicin, cytarabide, platinum salts, and bleomycin.

20. The method of claim 1, wherein the compound is administered to the subject in combination with an anti-inflammatory agent selected from dexamethasone, prednisolone, indomethacin, naproxene, ibuprofene celecoxib, methotrexate, adalimumab, infliximab and tocilizumab.

21. The method of claim 1, wherein the compound is administered to the subject in combination with an anti-neoplastic agent selected from doxorubicine, trametinib, sonidegib and durvalumab.

22. The method of claim 1, wherein the compound is administered in combination with an agent selected from pirfenidone, nintedanib and methotrexate.

23. The method according to claim 1, wherein the subject is a human.

* * * * *